(12) United States Patent
Brauers et al.

(10) Patent No.: US 9,179,863 B2
(45) Date of Patent: Nov. 10, 2015

(54) BED EXIT WARNING SYSTEM

(75) Inventors: Andreas Brauers, Aachen (DE); Kai Eck, Aachen (DE); Kurt Stadlthanner, Aachen (DE); Xavier L. M. A. Aubert, Brussels (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 368 days.

(21) Appl. No.: 13/063,005

(22) PCT Filed: Sep. 2, 2009

(86) PCT No.: PCT/IB2009/053818
§ 371 (c)(1),
(2), (4) Date: Mar. 9, 2011

(87) PCT Pub. No.: WO2010/029466
PCT Pub. Date: Mar. 18, 2010

(65) Prior Publication Data
US 2011/0156915 A1   Jun. 30, 2011

(30) Foreign Application Priority Data
Sep. 10, 2008   (EP) .................................. 08164045

(51) Int. Cl.
| | | |
|---|---|---|
| *G08B 23/00* | (2006.01) |
| *A61B 5/11* | (2006.01) |
| *A61B 5/02* | (2006.01) |
| *A61B 5/024* | (2006.01) |
| *G08B 21/04* | (2006.01) |
| *G08B 21/22* | (2006.01) |
| *A61B 5/01* | (2006.01) |
| *A61B 5/08* | (2006.01) |
| *A61B 5/00* | (2006.01) |

(52) U.S. Cl.
CPC .................. *A61B 5/1113* (2013.01); *A61B 5/02* (2013.01); *A61B 5/02405* (2013.01); *A61B 5/1115* (2013.01); *G08B 21/0461* (2013.01); *G08B 21/22* (2013.01); *A61B 5/01* (2013.01); *A61B 5/0816* (2013.01); *A61B 5/6887* (2013.01); *A61B 5/6892* (2013.01); *A61B 5/7267* (2013.01); *A61B 2560/0247* (2013.01)

(58) Field of Classification Search
None
See application file for complete search history.

(56) References Cited

U.S. PATENT DOCUMENTS

| | | | | |
|---|---|---|---|---|
| 6,067,019 A | * | 5/2000 | Scott ......................... | 340/573.4 |
| 7,316,171 B2 | | 1/2008 | Nemoto | |
| 7,336,187 B2 | * | 2/2008 | Hubbard et al. ........... | 340/573.1 |
| 7,547,279 B2 | * | 6/2009 | Kim et al. .................... | 600/300 |
| 7,629,890 B2 | * | 12/2009 | Sullivan et al. ............. | 340/573.1 |
| 7,656,299 B2 | * | 2/2010 | Gentry et al. ............... | 340/573.1 |
| 7,666,151 B2 | * | 2/2010 | Sullivan et al. .............. | 600/587 |

(Continued)

FOREIGN PATENT DOCUMENTS

| | | | |
|---|---|---|---|
| JP | 8275934 A | 10/1996 |
| JP | 8322813 A | 12/1996 |

(Continued)

*Primary Examiner* — John A Tweel, Jr.
*Assistant Examiner* — Adnan Aziz

(57) ABSTRACT

A bed exit warning system is used in monitoring a user on a bed that include one or more sensors for measuring one or more physiological characteristics of the user and for producing corresponding signals indicative of the one more physiological characteristics. A processor is configured to monitor the corresponding signals and to determine the likelihood that the user is about to get out of the bed from changes in the one or more physiological characteristics.

13 Claims, 2 Drawing Sheets

(56) References Cited

U.S. PATENT DOCUMENTS

| | | |
|---|---|---|
| 7,911,348 B2 * | 3/2011 | Rodgers ............... 340/573.1 |
| 8,109,874 B2 * | 2/2012 | Kong et al. ............ 600/300 |
| 8,123,685 B2 * | 2/2012 | Brauers et al. ......... 600/301 |
| 8,381,336 B2 * | 2/2013 | Kazuno et al. ......... 5/600 |
| 2003/0114736 A1 * | 6/2003 | Reed et al. ............ 600/300 |
| 2005/0124864 A1 * | 6/2005 | Mack et al. ............ 600/300 |
| 2006/0017153 A1 | 1/2006 | Choi |
| 2006/0049936 A1 * | 3/2006 | Collins et al. ......... 340/539.11 |
| 2006/0169282 A1 * | 8/2006 | Izumi et al. ........... 128/204.23 |
| 2007/0118054 A1 * | 5/2007 | Pinhas et al. .......... 600/587 |
| 2007/0132597 A1 | 6/2007 | Rodgers |
| 2007/0156031 A1 | 7/2007 | Sullivan |
| 2007/0276202 A1 | 11/2007 | Raisanen |
| 2008/0005838 A1 | 1/2008 | Fong |
| 2008/0169931 A1 * | 7/2008 | Gentry et al. .......... 340/573.1 |
| 2008/0269625 A1 * | 10/2008 | Halperin et al. ........ 600/508 |
| 2009/0119843 A1 * | 5/2009 | Rodgers et al. ........ 5/611 |
| 2009/0260158 A1 | 10/2009 | Kazuno |
| 2011/0034811 A1 * | 2/2011 | Naujokat et al. ....... 600/484 |

FOREIGN PATENT DOCUMENTS

| | | |
|---|---|---|
| JP | 2001057996 A | 3/2001 |
| JP | 2004180804 A | 7/2004 |
| JP | 2007097966 A1 | 4/2007 |
| JP | 2007330336 A | 12/2007 |
| WO | 2004006768 A1 | 1/2004 |
| WO | 2004073577 A1 | 9/2004 |

* cited by examiner

BED EXIT WARNING SYSTEM

TECHNICAL FIELD OF THE INVENTION

The invention relates to a bed exit warning system, and in particular relates to a bed exit warning system that monitors vital signs of the user of the system.

BACKGROUND TO THE INVENTION

It is important in several applications to monitor whether a user or patient is in their bed, or whether the user or patient has got up and left their bed. The most prominent applications are the care of the elderly, care of children and care of patients with specific conditions or circumstances, for example post-surgery.

There are several prior art devices available that can detect when a patient has left their bed. Usually, these devices use either pressure switches or pressure sensing mats on the bed, with the relieving of pressure being associated with the patient leaving the bed.

For many of these devices, reliable operation requires the pressure switch or pressure sensing mat to be installed on top of a mattress on the bed. This results in two major shortcomings. Firstly, the devices are often stiff (i.e. resistant to flexing), which causes discomfort to the occupant of the bed, and which, in some applications (for example, in the monitoring of patients with dementia) can cause physical and psychological irritation to the patient. Secondly, because the devices are placed on top of the (flexible) mattress, they can rapidly suffer material fatigue and fail under normal use.

Furthermore, it is clear from the nature of the applications that it is desirable to provide an alarm that the patient or user has left the bed as early as possible, whilst minimizing the occurrence of false alarms.

Conventional devices predict bed exits by a user using pressure sensitive mats with a spatial resolution. Thus, with these mats, a repositioning of the bed occupant is detected as a change in the weight distribution over the surface of the mat. Usually, an alarm can be triggered when the detected position of the bed occupant exceeds some predefined thresholds. However, as these devices rely on the use of large pressure sensitive mats (i.e. the size of, or close to the size of, the bed), they are quite intrusive.

Therefore, it is an object of the invention to provide an alternative system for predicting when a user is going to get out of bed.

SUMMARY OF THE INVENTION

Therefore, according to a first aspect of the invention, there is provided a bed exit warning system for use in monitoring a user on a bed, the system comprising one or more sensors for measuring one or more physiological characteristics of the user and for producing corresponding signals indicative of the one or more physiological characteristics; and a processor adapted to monitor the corresponding signals and to determine the likelihood that the user is about to get out of the bed from changes in the one or more physiological characteristics.

Preferably, the processor is further adapted to issue an alarm or warning signal in the event that it determines that the user is likely to get out of the bed.

In preferred embodiments, the one or more physiological characteristics of the user measured by the one or more sensors comprise any one or more of heart rate, pulse rate, breathing rate, temperature, blood pressure or heart rate variability.

Preferably, the processor is adapted to determine whether the user is about to get out of the bed by comparing the changes in the one or more physiological characteristics to a set of predetermined thresholds or criteria.

Preferably, the processor is adapted to determine the likelihood that the user is about to get out of the bed by comparing changes in the one or more physiological characteristics to data collected during a number of preceding bed exits by the user.

In preferred embodiments, the bed exit warning system comprises a sensor for detecting the presence or absence of the user on the bed.

Preferably, one of the one more sensors for measuring physiological characteristics is used as the sensor for detecting the presence or absence of the user on the bed.

In one embodiment, the sensor comprises a pressure sensor or strain gauge.

Preferably, the processor is further adapted to issue an alarm or warning signal in the event that the sensor indicates that the user has got out of the bed.

Preferably, the processor is adapted to determine the likelihood that the user is about to get out of the bed from changes in the one or more physiological characteristics using a bed exit prediction algorithm.

Preferably, the processor is adapted to update the bed exit prediction algorithm based on a comparison between the determined likelihood and an indication of whether the user subsequently exits the bed from the sensor.

Preferably, the processor comprises a supervised classification algorithm for implementing the bed exit prediction algorithm.

According to a second aspect of the invention, there is provided a method of predicting the likelihood of a user getting out of bed, the method comprising monitoring one or more physiological characteristics of the user; and determining the likelihood that the user is about to get out of the bed from changes in the one or more physiological characteristics.

According to a third aspect of the invention, there is provided a computer program product for predicting the likelihood of a user getting out of bed, the computer program product comprising computer program code that, when executed on a computer or processor, causes the computer or processor to receive signals indicative of one or more physiological characteristics of a user; and determine the likelihood that the user is about to get out of the bed from changes in the one or more physiological characteristics indicated by the received signals.

Therefore, the invention provides a system and method for predicting when a monitored subject is going to get out of bed, based on physiological characteristics of the subject. The reliability of the prediction of bed exit is evaluated to minimize false positive alarms. The system can further provide a warning or alarm in the event that the monitored subject does get out of the bed. The system has the advantage that it is completely unobtrusive to the monitored subject.

BRIEF DESCRIPTION OF THE DRAWINGS

Various embodiments of the invention will now be described, by way of example only, with reference to the following drawings, in which.

DETAILED DESCRIPTION OF THE PREFERRED EMBODIMENTS

Figure 1:
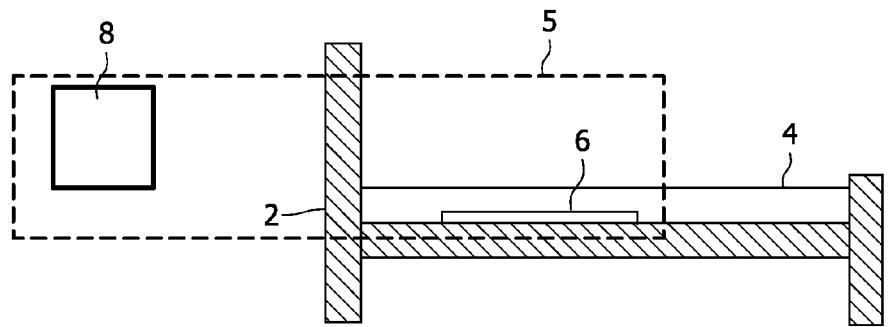
FIG. 1 is an illustration of a bed exit warning system in accordance with the invention.

In FIG. 1, a bed 2 is shown that has a mattress 4. A bed exit warning system 5 is provided for predicting when a person laying on the mattress 4 is likely to get out of the bed 2. In this illustrated embodiment, the bed exit warning system 5 comprises a sensor unit 6 that is provided beneath the mattress 4, but in alternative embodiments, the sensor unit 6 may be provided on top of the mattress 4, or as an integral part of the bed 2, or integrated into the mattress 4.

The bed exit warning system 5 also comprises a base station 8, which can be located near to the bed 2 or further away at a monitoring station (such as a nurse's station, for example), that communicates with the sensor unit 6, and which can sound an alarm or warning that a person on the bed 2 is likely to get out of the bed 2.

Figure 2:
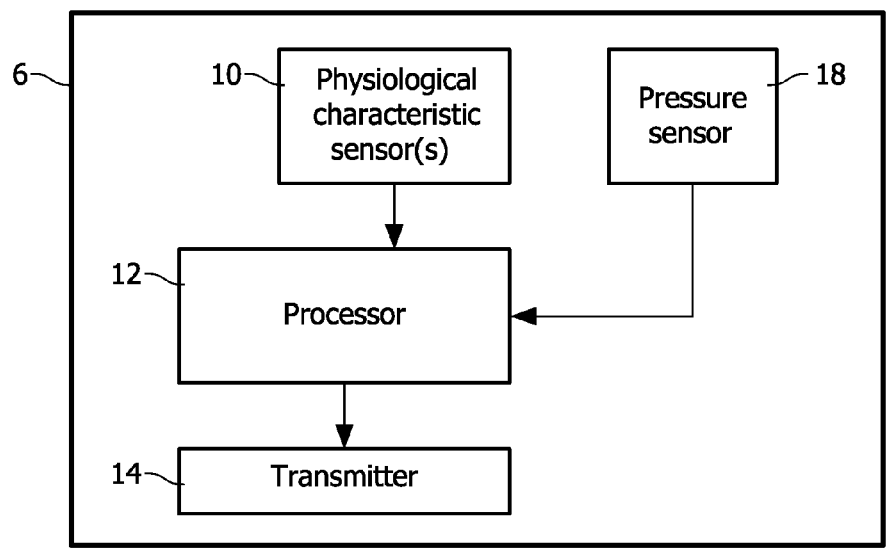
FIG. 2 is a block diagram of a bed exit warning system in accordance with the invention.
Figure 2:
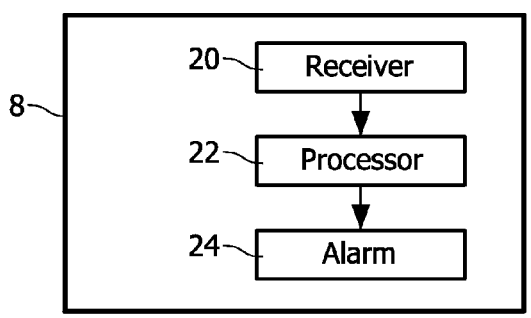

FIG. 2 shows the bed exit warning system 5 in more detail. The sensor unit 6 comprises one or more physiological characteristic sensors 10 that generate signals corresponding to physiological characteristics measured from the user. The physiological characteristics can comprise vital signs, such as pulse (or heart rate), temperature, blood pressure and breathing rate, or any other measurable physiological characteristics, such as heart rate variability. The one or more physiological characteristic sensors 10 can be passive sensors (i.e. not requiring a power supply) or active (i.e. requiring a power supply).

A processor 12 receives the signals from the one or more sensors 10 and monitors the signals to determine whether a user is about to get out of the bed 2. In particular, the processor 12 determines that a user is about to get out of the bed 2 in response to particular changes in the signals corresponding to the one or more physiological characteristics.

If the processor 12 does determine that the user is likely to get out of bed, a warning or alarm signal is provided to a transmitter 14 that transmits the warning or alarm signal to the base station 8.

In preferred embodiments, the sensor unit 6 also comprises a sensor 18 for detecting that the user has actually got out of the bed 2. This sensor 18 can comprise at least one pressure sensor or strain gauge which allows the system 5 to determine whether the user has got out of the bed 2. In addition, if the pressure sensor or strain gauge has a spatial dimension (i.e. it can determine where on the bed pressure or strain is being exerted), this can be used by the processor 12 as part of the determination of whether the user is going to get out of the bed 2. The sensor 18 can also or alternatively comprise a sensor or sensors for measuring ambient conditions around the user or bed 2.

In a preferred embodiment, one of the sensors 10 used for measuring physiological characteristics of the user can be used in place of a separate sensor 18 for detecting that the user has actually got out of the bed. For example, a sensitive pressure sensor or strain gauge can be used to measure a heart beat or heart rate, and this pressure sensor or strain gauge can also be used to detect that the user is still in the bed.

The base station 8 comprises a receiver 20 for receiving the warning or alarm signal from the sensor unit 6, a processor 22 and an alarm 24 for issuing an alarm or warning that the user is about to get out of the bed 2.

It will be appreciated that, in alternative embodiments, the prediction of a bed exit can be made in the base station 8 rather than the sensor unit 6, in which case the sensor unit 6 transmits the signals from the sensors 10 to the base station 8 for analysis.

It will be further appreciated that the functions of the sensor unit 6 and base station 8 can be integrated into a single device.

The sensor unit 6 can continuously monitor the physiological characteristics, such as movements, breathing rate and heart rate (including heart rate variability). The processor 12 can use the resulting signals to predict a bed exit event as described below.

Figure 3:
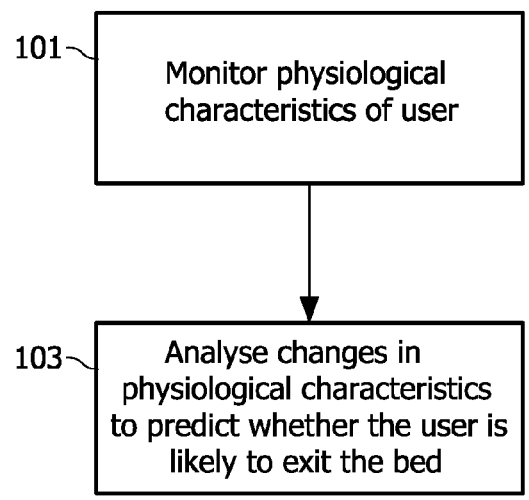
FIG. 3 is a flow chart illustrating a method in accordance with the invention.

FIG. 3 shows a method in accordance with a first aspect of the invention. In step 101, physiological characteristics of a user of the bed 2 are monitored. In step 103, changes in the physiological characteristics of the user are analyzed using a bed exit prediction algorithm to predict whether the user is likely to get out of the bed. The bed exit prediction algorithm can, in a simple embodiment, comprise a set of thresholds or criteria for the physiological characteristics of the user, or a set of thresholds or criteria for changes in the physiological characteristics of the user.

It has been observed that a typical "bed exit" event at night has four distinct stages: the person wakes up, the person notices an urge to go to the toilet (or another reason to get out of bed), the person sits up in the bed, and the person gets out of the bed.

It is well known that the process of waking up is reflected by a heart rate variability of individuals, as well as in the activity spectrum. Thus, the processor 12 in the sensor unit 6 can recognize this variability from the signals provided from the physiological characteristic sensors 10, even before the individual has necessarily made a conscious decision to get out of the bed. When the person does decide to get up, a "sympathetic activation" will be measured, which results in another change in the heart rate variability pattern. When the person sits up in bed this will on the one hand result in a significant change of forces acting on the pressure sensor or strain gauge (if present), and the heart rate will go up due to the change of posture into a vertical position. Then the person will leave the bed, which means that physiological characteristics will no longer be detected, and the pressure sensor or strain gauge (if present) will indicate that the bed 2 is not occupied.

Although the bed exit system 5 measures a set of physiological characteristics that indicate the process of getting out of bed, it can also reliably detect the actual bed exit, once it has happened. This makes it possible for the system 5 to be self-learning, which means that the system 5 can analyze the changes in the physiological characteristics that occur before an actual bed exit and to tailor the algorithm used to determine whether a bed exit is likely to take place to a particular user or patient.

Thus, preferred embodiments of the invention use such recurrent learning to adapt the bed exit prediction algorithm, as even if some of the steps carried out in the bed exit process (such as waking up, sitting up) always occur, they may still vary from individual to individual in some respects (such as duration from sitting up to getting out of the bed, etc.).

The recurrent learning system could be implemented in the form of a probability network, which receives the physiological characteristic values and outputs from other sensors (such as heart rate variability, large movements, amount and/or location of pressure, breathing rate and heart rate).

The system 5 could evaluate the probability of a bed exit according to the data of a specific person recorded during the last n bed exits. This system would therefore automatically adapt to changes in the behavior of the monitored person, which may be caused by various factors, such as a change in medication or an improvement or decline in their physical condition.

Figure 4:
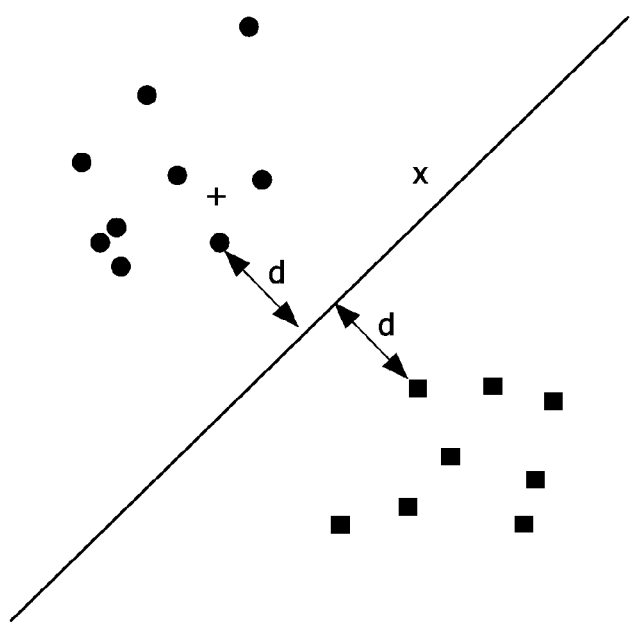
FIG. 4 shows a support vector machine classification for predicting a bed exit.

The way to provide this recurrent learning system is to train some classifier like a neural network (NN)or a support vector machine (SVM), These supervised classification algorithms learn from training pairs consisting of the acquired data plus the knowledge that a bed exit had indeed occurred. In this context, support vector machines are preferred over neural networks, as SVMs try to find a separating hyper plane between the two classes of objects to be separated (see FIG. 4). This hyper plane (shown as the black solid line in FIG. 4) is constructed such that it has the largest possible distance d to the two closest objects of the two classes to be separated. New points are assigned to the classes depending on their position with respect to the separation hyper plane. Points that lie close to the separating hyper plane (for example the "x" point) are less reliably classified than points with a larger distance from the hyper place (for example the "+" point). Accordingly, the reliability of a bed exit alarm can be evaluated directly, a property which can be used advantageously to decrease the number of false positive alarms.

Furthermore, having a reliability measure can provide advantages in typical applications, such as in an elderly care home, where it is up to a night nurse to decide on whether to follow up on a "predictive" alarm (i.e. an alarm predicting a bed exit). The application could be designed in a way that for every individual person the reliability level that leads to a notification to the care staff can be adjusted to the personal needs of the patient.

Therefore, there is provided a bed exit warning system that provides a reliable prediction of whether a user/patient is about to get out of bed based on changes in measurements of physiological characteristics and which, in preferred embodiments, provides a reliable bed presence detector, and which can adapt to individual characteristics of the user/patient automatically to predict a bed exit. An important aspect of this prediction is that it can be tagged with a reliability score in order to optimize the use of the system as an alarming system for example in dementia care or hospital care.

As described above, the bed exit warning system 5 unobtrusively monitors physiological characteristics of the person on the bed 2, and (in preferred embodiments) ambient conditions and the actual presence or absence of the user in the bed 2.

The system 5 also has the advantage that a combination of physiological characteristic monitoring with pressure or strain sensing allows a user in distress to be detected (i.e. distress in the sense that they have stopped breathing, they have an abnormal heart rate (i.e. too slow (bradycardia) or too fast (tachycardia) or irregular (arrhythmia)) or their temperature has dropped or increased), and a separate alarm signal generated.

Thus, the invention provides a system for predicting when a user is going to get out of bed. Furthermore, preferred embodiments of the invention provide a system that is fully unobtrusive, and does not impact on the comfort of the user in any way.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A bed exit warning system for monitoring a user on a bed including a mattress, the system comprising:
   a base station configured to issue a warning that the user is about to get out of the bed;
   one or more sensors placed in a position selected from one of beneath the mattress and in the mattress, and configured to continuously and directly measure one or more physiological characteristics of the user; and
   a processor configured
     to determine a likelihood that the user is about to get out of the bed from changes in the measured one or more physiological characteristics, and
     to notify the base station of the likelihood,
   wherein the processor is configured to determine the likelihood by comparing the changes in the measured one or more physiological characteristics to previously collected one or more physiological characteristics during which bed exits by the user occurred.

2. The bed exit warning system as claimed in claim 1, further comprising a transmitter configured to transmit a signal to notify the base station of the likelihood, wherein the base station includes a receiver configured to receive the signal, and wherein the processor comprises a first processor connected to the one or more sensors and the transmitter, and a second processor connected to the base station and the receiver.

3. The bed exit warning system as claimed in claim 1, wherein the measured one or more physiological characteristics comprise at least one of heart rate, pulse rate, breathing rate, temperature, blood pressure and heart rate variability.

4. The bed exit warning system as claimed in claim 1, wherein the processor is further configured to determine the likelihood by comparing the changes in the measured one or more physiological characteristics to a plurality of predetermined thresholds for the measured one or more physiological characteristics.

5. The bed exit warning system as claimed in claim 1, further comprising an absence sensor configured to detect the presence or absence of the user on the bed.

6. The bed exit warning system as claimed in claim 5, wherein the absence sensor is one of the one or more sensors configured to continuously measure the one or more physiological characteristics.

7. The bed exit warning system as claimed in claim 5, wherein the absence sensor comprises at least one of a pressure sensor and strain gauge.

8. The bed exit warning system as claimed in claim 5, wherein the warning is issued when the absence sensor indicates that the user is absent from the bed.

9. The bed exit warning system as claimed in claim 1, wherein the changes in the measured one or more physiological characteristics are determined using a bed exit prediction algorithm.

10. The bed exit warning system as claimed in claim 9, wherein the bed exit prediction algorithm is updated based on a comparison between the determined likelihood and an indication of the user is subsequently getting out of the bed.

11. The bed exit warning system as claimed in claim 9, wherein a supervised classification algorithm implements the bed exit prediction algorithm.

12. A method of predicting a likelihood of a user getting out of bed including a mattress, the method comprising the acts of:
   placing one or more sensors in a position selected from one of beneath the mattress and in the mattress, and continuously and directly measuring one or more physiological characteristics of the user;
   determining the likelihood that the user is about to get out of the bed from changes in the measured one or more physiological characteristics; and
   issuing a notification of the likelihood,
   wherein the determining act determines the likelihood by comparing the changes in the measured one or more physiological characteristics to previously collected one or more physiological characteristics during which bed exits by the user occurred.

13. A non-transitory computer readable medium comprising computer code that, when executed on a computer performs a method of predicting a likelihood of a user getting out of bed including a mattress, the method comprising acts of:
   causing one or more sensors placed in a position selected from one of beneath the mattress and in the mattress to continuously and directly measure one or more physiological characteristics of the user;
   determining the likelihood that the user is about to get out of the bed from changes in the measured one or more physiological characteristics; and
   issuing a notification of the likelihood,
   wherein the determining act determines the likelihood by comparing the changes in the measured one or more physiological characteristics to previously collected one or more physiological characteristics during which bed exits by the user occurred.

\* \* \* \* \*